United States Patent

Wood

[11] Patent Number: 5,892,140
[45] Date of Patent: Apr. 6, 1999

[54] MICROMACHINED INFERENTIAL OPTO-THERMAL GAS SENSOR

[75] Inventor: R. Andrew Wood, Bloomington, Minn.

[73] Assignee: Honeywell Inc., Minneapolis, Minn.

[21] Appl. No.: 846,724

[22] Filed: Apr. 30, 1997

[51] Int. Cl.[6] .............................. G01N 7/00; H01J 5/02
[52] U.S. Cl. ......................... 73/310; 73/31.5; 250/338.1
[58] Field of Search ................. 73/23.2, 23.31, 73/31.05; 250/343, 338.1; 356/437

[56] References Cited

U.S. PATENT DOCUMENTS

| | | | |
|---|---|---|---|
| 4,500,207 | 2/1985 | Maiden | 356/409 |
| 4,694,173 | 9/1987 | Wong | 250/343 |
| 4,727,006 | 2/1988 | Malinowski et al. | 429/50 |
| 4,738,266 | 4/1988 | Thatcher | 128/719 |
| 5,053,754 | 10/1991 | Wong | 340/632 |
| 5,081,998 | 1/1992 | Yelderman et al. | 128/719 |
| 5,444,249 | 8/1995 | Wong | 250/343 |
| 5,464,983 | 11/1995 | Wang | 250/343 |
| 5,550,375 | 8/1996 | Peters et al. | 250/343 |
| 5,589,689 | 12/1996 | Koskinen | 250/339.01 |
| 5,600,148 | 2/1997 | Cole et al. | |
| 5,646,729 | 7/1997 | Koskinen et al. | 356/352 |
| 5,650,624 | 7/1997 | Wong | 250/338.5 |
| 5,691,704 | 11/1997 | Wong | 340/628 |

FOREIGN PATENT DOCUMENTS 1352977  of 0000  United Kingdom.
9008952A  8/1990  WIPO.

OTHER PUBLICATIONS

Patent Abstracts of Japan, vol. 097, No. 008, 29 Aug. 1997 & JP 09 089773A (Horiba Ltd), 4 Apr. 1997, See Abstract.

Primary Examiner—Hezron Williams
Assistant Examiner—Jay L. Politzer
Attorney, Agent, or Firm—John G. Shudy, Jr.

[57] ABSTRACT

A micromachined integrated opto-thermal sensor having a rapidly intensity varying or pulsing light source, an interference filter, shadow masking or reflective blocking of light from thermal sensors, or differential operation, a gas cavity into which the detected gas can flow into via a channel or filter, and a thermal detector elements to sense the heating of the gas caused by the absorption of light at a particular wavelength by the specific gas to be detected. Another version of the sensor is one with a dual cavity. One cavity contains the gas to be detected and the other cavity is sealed from the ambient environment and contains no gas. Signals from the detectors from the cavities are subtracted from each other resulting in the elimination of a fixed signal due to radiation impinging the detectors.

25 Claims, 6 Drawing Sheets

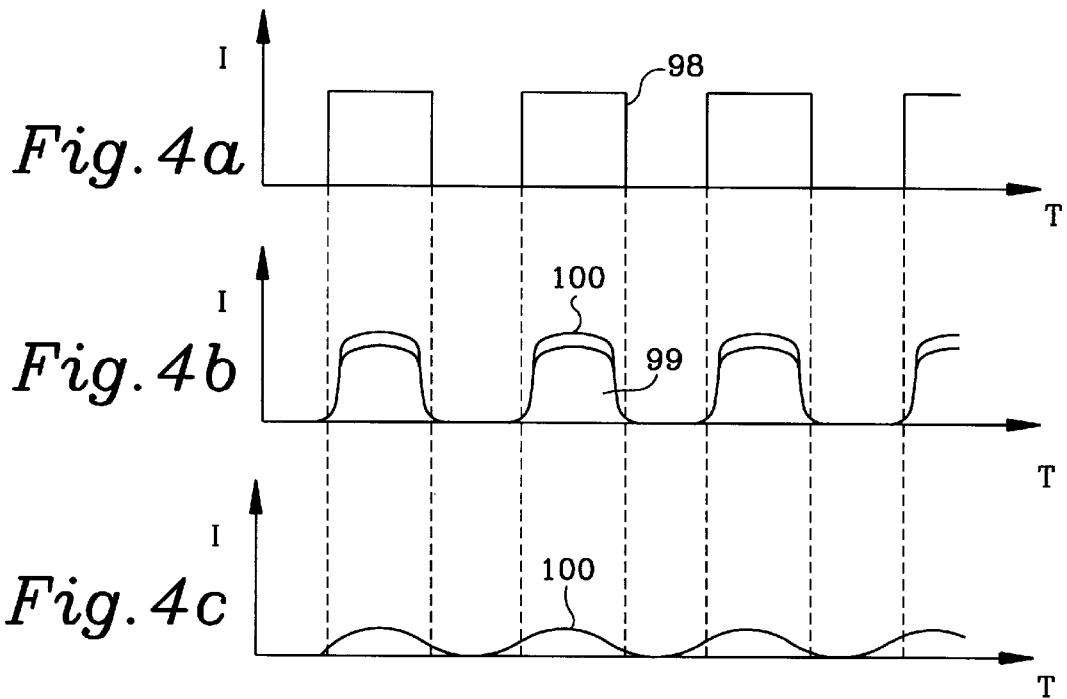
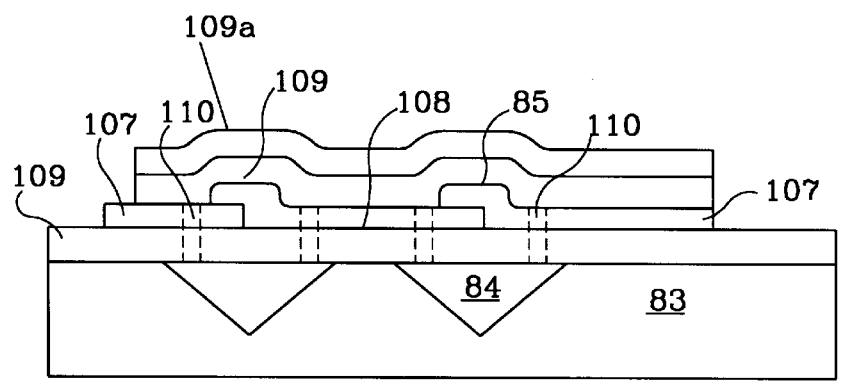

MICROMACHINED INFERENTIAL OPTO-THERMAL GAS SENSOR

BACKGROUND

The invention pertains to gas sensors and particularly to toxic gas sensors. More particularly, the invention pertains to micromachined integrated circuit gas and fluid sensors.

Related art devices for sensing toxic gases such as CO, $CO_2$, NO, $NO_2$ and VOCs generated by combustion processes have been based on sensors indicating changes in metal oxide film conductivity, chemiluminescence, fluorescence, various forms of IR absorption, and so forth. These sensors have been either too costly, unstable, or insensitive to meet the requirements of a low-cost, reliable toxic gas sensor. Their sensing such toxic gases in concentrations that are commensurate with the levels at which they can be harmful to health and life is difficult, especially if it is to be done via low-cost, affordable and reliable sensors. Often the older gas engines or heaters, operated by budget-minded users, are most likely to be a source of toxic gases which endanger these users and others. These users are the ones most unlikely to buy toxic gas indicators, unless someone manages to bring affordable and appropriate technology to them.

Optoacoustic gas sensors sense low concentrations of gases by inducing a gas temperature variation by narrow-band modulated illumination at a wavelength which the gas absorbs. The modulated temperature signal is not sensed directly, but a closed or nearly-closed gas sample cell is used which converts the small gas temperature signals into a pressure signal, which is detected by a microphone. A closed or nearly-closed gas cell makes it difficult for gas to enter and exit the gas cell.

SUMMARY OF THE INVENTION

Direct sensing of the gas temperature modulation signal, which is called optothermal sensing, removes the need for a closed or nearly-closed gas cell. The direct sensing of the gas temperature signal is handicapped by a lack of a suitably sensitive (i.e., nanodegree sensitivity) and fast-response gas temperature sensor. The use of a micromachined thermoelectric sensor array does allow suitably sensitive, fast response detection of the small gas temperature modulation signal. Such arrays are conveniently fabricated by silicon micromachining.

The present invention provides a new, useful, low-cost and reliable direct sensing of the gas temperature signal of the present gas, and also provides the inferred indication of the presence of a toxic gas or objectionable constituents of combustion products. It is not necessary to directly measure the toxic or objectionable gases, if one can identify a phenomenon that would indicate or infer their presence with a meaningful probability level. The present sensor thus provides more compact, reliable, affordable detection than direct NDIR sensing of toxic gases. It also provides additional detection/alarm protection against high $CO_2$ or other gas concentrations by direct sensing.

The sensor takes advantage of the indirect indication of toxic combustion products, such as CO, $NO_x$ and VOCs via $CO_2$ detection, and a low-cost, integrated gas sensor design is thus made available at a reasonable price to meet the toxic gas sensing needs of users of unvented space heaters (or kitchen stoves) and the needs of automobile drivers that wish to detect exhaust fumes from cars or near them.

Carbon dioxide ($CO_2$) indicates the presence of objectionable concentrations of combustion products. $CO_2$ is generated by combustion processes, in concentrations that are 10 to 100 times higher than those of CO, $NO_x$ or VOCs. Yet one can measure $CO_2$ at concentration levels that are 3 to 30 times lower than the above-noted gases, especially via NDIR. Combustion products, especially those from gasoline or diesel fuel are known to consist of 5–15% $CO_2$, 10–20% $H_2O$, 0–10% $O_2$, 70–80% $N_2$, 0.001 to 0.4% $NO_x$, 0.001 to 0.2% CO (CO in worn or maladjusted automotive engines may be up to 2%), and 0.001 to 0.3% hydrocarbons (HC), i.e., $CO_2$ concentrations always predominate. Still, dilution of exhaust gas of the car in front is expected to be 10 to 1000-fold before reaching the cabin air intake of the following car, so that the $CO_2$ concentration is likely to be only 0.005 to 1.5%, which is measurable, while the toxic gas concentration is in the 0.0001 to 0.04% range. The latter concentrations are much more difficult to measure, and especially so with low-cost sensors, which would often not begin to sense those gases in spite of being present in concentrations that cause discomfort or adverse health effects.

A signal from temperature detectors or thermal sensors of the opto-thermal sensor, indicating an amount of concentration of the gas or fluid having an absorption wavelength at the first wavelength, goes to a processor. The processor processes the signal from said detector and provides inferred information indicative of a presence of other gases or fluids and/or future or present or past chemical or physical activity.

The processor contains a table of information that indicates certain amounts of concentrations of particular gases or fluids to infer the presence of certain amounts of concentrations of, for example, certain combustion products. As noted above, the presence of certain amounts of concentrations of combustion products are more accurately inferred by the presence of certain amounts of concentrations of the particular gases or fluids because the latter amounts of concentrations are up to several magnitudes larger than the detected certain amounts of concentrations of combustion products.

The processor may be connected to an output of a lock-in amplifier, which is connected to the sensor output, wherein the processor can infer the presence of amounts of concentrations of other gases and/or fluids based on the signal at the output of said lock-in amplifier, for a given first wavelength of radiation provided by the emitter, to impinge the gas or fluid present in the cavity of the opto-thermal sensor. For instance, if the first wavelength were set at an absorption wavelength of $CO_2$, then there would be direct detection of the presence of $CO_2$ for inferred detection of the presence of particular combustion products.

The integrated design of the present sensor enhances its manufacturability and affordability. The gas cell, thermal detector and optical filter are integrated into one compact micromachined unit which is of lower cost, i.e., more affordable and more widely applicable than higher cost sensors. Infrared radiation may be obtained from small light bulbs, or from electrically heated microbridges (microemitters). Electronic circuits may also be integrated into the silicon material. The sensors are more compact and therefore more rugged, and overall more useful. The integrated opto-thermal sensor used as the detector of the present gas results in a more sensitive, faster response and more stable detection. The faster response is because a closed or nearly closed gas cell is not required.

The integrated sensor is 10 to 100 times smaller than the related art sensors, which makes the present system more affordable, portable and useful. The present detectors are also 10 to 100 times less costly than the related-art detectors because they can be mass-produced using silicon micromachining.

The present highly accurate gas detector is formed from micromachined silicon technology thereby being much smaller than related-art detectors.

In summary, the invention is a low-cost opto-thermal sensing system, which is a micromachined integrated sensor, which has a pulsing, heated radiation source, an appropriate multi-layer interference filter (IF), anti-reflective (AR) film, shadow masking or reflective blocking to prevent light from impinging thermal sensors, and specially etched silicon wafer or masking designed to maximize the infrared red (IR) or light of other wavelengths, to provide energy efficiency at, for instance the 4.3 micron wavelength band of $CO_2$, a sample gas cavity into which gas can flow in and out via channels, or diffuse in and out the etch holes used earlier in fabrication to dissolve the sacrificial layer utilized to form the cavity or via a porous compressed stainless steel frit, and a micromachined gas temperature sensor, operated in single-output or differential-output manner.

The effect of slow ambient temperature variations on the sensor are naturally rejected by a thermoelectric junction-pair arrangement. The effect of gas temperature variations caused by air and/or gas drafts may be minimized by suitable porous baffles, and by lock-in detection. To minimize background signals, the thermoelectric temperature sensors may be not directly illuminated by the optical radiation, and may be coated with a reflective material, and may be operated in a differential manner by placing suitable IFs between the optical illuminator and the gas temperature sensors, and a suitable gas inlet arrangement.

BRIEF DESCRIPTION OF THE DRAWING

FIGS. 4a, 4b and 4c are waveform diagrams of light and heat signals of a thermal sensor.

FIG. 5 is a diagram of the structure of a thermal sensor element.

DESCRIPTION OF THE EMBODIMENTS

Figure 1:
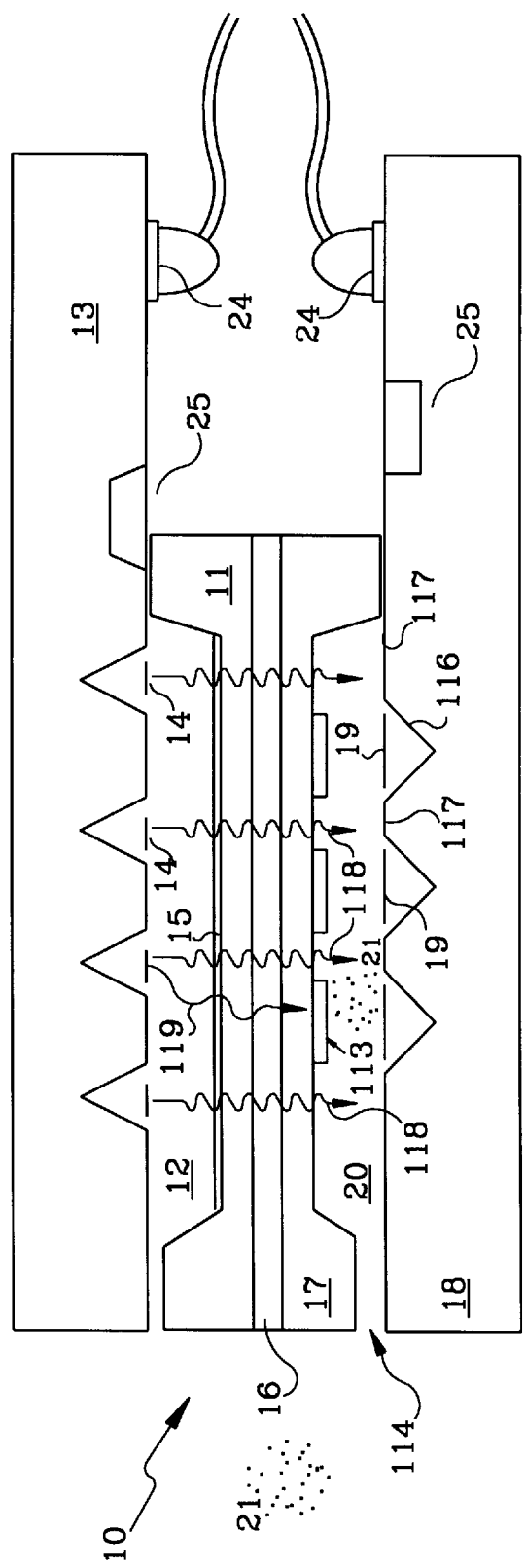
FIG. 1 shows a micromachined inferential opto-thermal gas sensor.

FIG. 1 is a diagram that shows a basic structure of inferential opto-thermal gas sensor 10. Silicon wafer 11 has an etched space 12 on one side. On that side having depression 12 is formed a silicon wafer 13 having a set of microemitters 14 on the side adjacent to wafer 11. Formed on the surface or side of wafer 11 adjacent to microemitters 14 is an antireflective (AR) coating 15. On the other side of wafer 11 is a narrow band pass interference filter (IF) 16 designed to pass only infrared light having a wavelength that is the same as the absorption wavelength (4.3 microns) of $CO_2$. The AR and IF coatings or films may be interchanged in location with each other. Silicon wafer 17 is formed on filter 16. Silicon wafer 18 is formed on wafer 17. Silicon wafers 17 and 18 are etched to form a cavity 20 and channels 114. Channels 114 form a pathway between cavity 20 and the ambient volume or space external to sensor 10. Gas or air 21 can diffuse or flow in and out of cavity 20 via orifice, path or channels 114. Wafer 18 has thermal sensors 19 formed over pits 116. Microemitters 14 and thermal sensors 19 are connected to contact pads 24. Formed on wafer 13 or 18 may be an integrated circuit (IC) or an application specific integrated circuit (ASIC) for providing electronics 25 for controlling microemitters 14 or processing signals from thermal sensors 19. Wafer 11 may be substituted with a glass plate. Even wafer 17 may be substituted with glass. In the embodiments disclosed below, the IF filter and the AR coating may be situated or formed on glass, also.

Radiation source 14 is a 32×32 array of microemitters that function as an infrared radiation source. Array 14 provides total emission at 4.3 microns about 2.8 times that of a mini-tungsten light bulb. Cavity 20 is about 100 microns deep×500 microns wide. Cavity 20 cannot be too small or gas cooling at cavity surfaces would reduce the sensitivity of gas sensor 10.

The thermal sensor is a 64×64 array of series-connected NiFe:Cr thermoelectric sensors 19, each having two thermoelectric metallic junctions per each 50 micron×50 micron silicon nitride microbridge, one junction on the microbridge and one on the adjacent silicon, with 10 ohms resistance per junction-pair, and a junction pair Seebeck coefficient of 60 microvolts/degree C. The thermoelectric sensors 19 are coated with a reflective metal layer to minimize direct absorption of infrared radiation. The thermal sensor has a typical microbridge response time of 0.5 millisecond and a 10 Hz illumination modulation. The lock-in electronics detection system (for example, amplifier 102, power source 104 and lock-in amplifier 103 in FIG. 3 with source elements 94 instead of lamp 93) has a 30 second response time (i.e., bandwidth dF=0.02 Hz). The rms. voltage noise=square root of (4 KT(64×64)RdF)=2.5 nanovolt rms. and sensitivity= (2.5e-9)/(64×64×60e-6)=10 nanodegree C. rms. This allows detection of typical gas temperature signals from a $CO_2$ concentration of about 100 ppm.

Figure 6A:
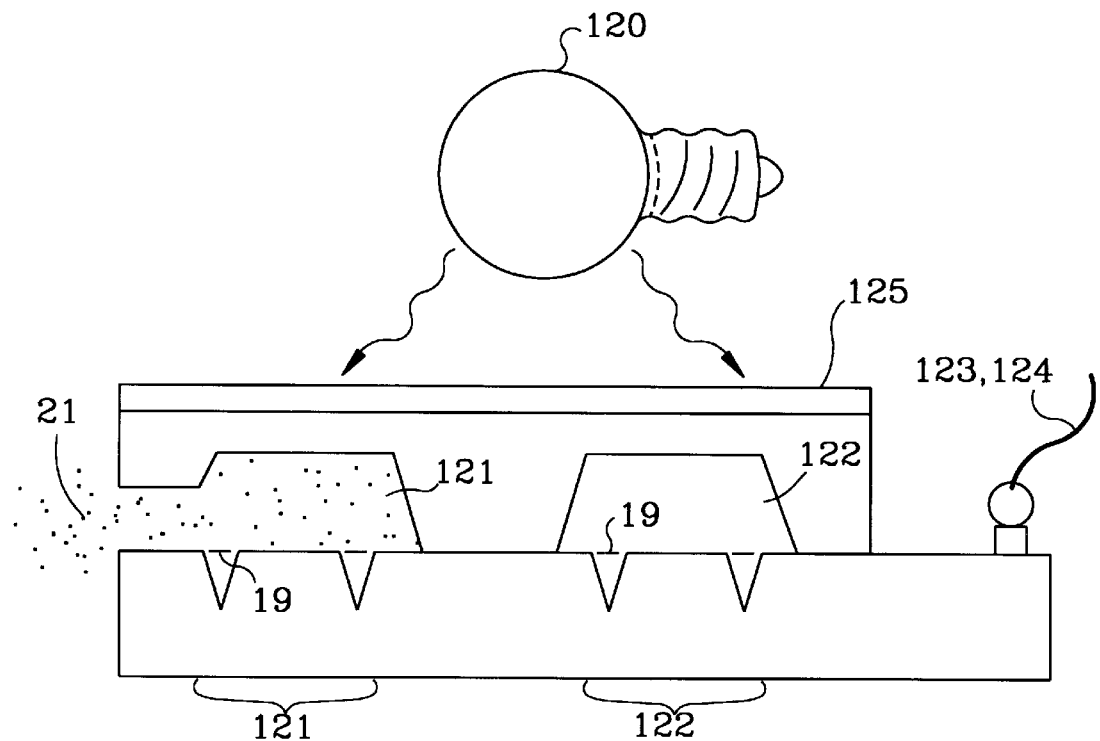
FIGS. 6a, 6b, 6c and 6d show a sensor operation in a differential manner.
Figure 6B:
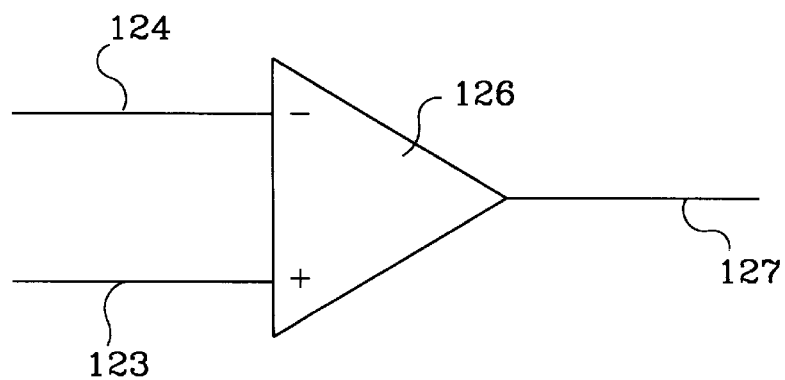

In FIG. 1, source 14 emits light 118 and 119. Light 119 is blocked by shadow masks 113. Light 118 goes through layer 15 and wafer 11. Only light 118 having a wavelength that is passed by narrow band pass interference filter 16 enters cavity 20 and is able to impinge air and/or gas 21 molecules. If such gas 21 has an absorption wavelength that is the same wavelength of light 118 that passes through filter 16 and impinges gas 21, then that light 118 is absorbed by gas 21 and gas 21 heats up. The increase of the temperature of gas 21 is sensed by thermal sensors 19, which output signals indicative of the presence of gas 21. Light 118 that is not absorbed by gas 21 impinges non-thermal areas 117 and does not affect sensors 19. Little light 118 or 119 will hit sensors 19 because of shadow masks 113. Light 119 from source 14 passes through film 15, wafer 11 and narrow band pass filter 16, and impinges masks 113. Masks 113 largely block light 119 that would otherwise enter cavity 20 and impinge thermal sensors 19. Impingement of sensors 19 by light 119 would cause sensors 19 to warm up and provide fixed signals not indicating presence of a gas. If light 119 impinged sensors 19, electronics may be used to remove fixed signals caused by such light 119 and pass only true signals indicating the presence of gas 21. This method of operation requires very stable electronics to remove the fixed signals. An alternative approach in FIG. 6a is to employ two arrays, 121 and 122, of thermal sensors 19, both illuminated by the same radiation source 120 through infrared filter 125 with one array 121 exposed to gas 21 and the other array 122 not exposed to gas 21. In FIG. 6b, two signals 123 and 124 from two arrays 121 and 122, respectively, may then be electronically subtracted to give a signal 127 by a differential amplifier 126 to substantially remove the fixed signals caused by impingement of thermal sensors or temperature detectors 19 by radiation.

Figure 6C:
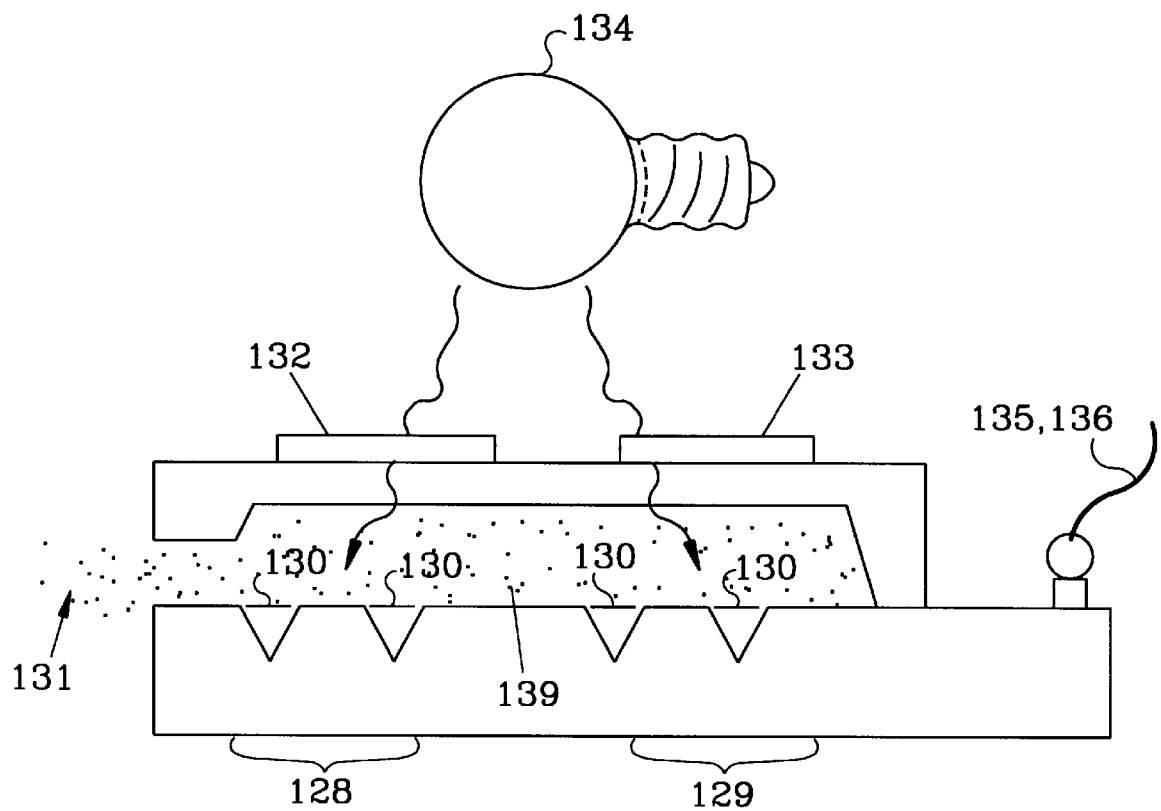
Figure 6D:
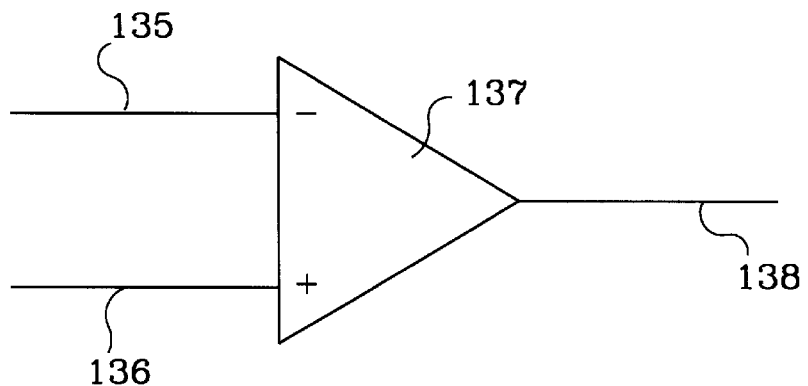

FIG. 6c shows another differential approach, in which two arrays 128 and 129 of thermoelectric sensors 130 in a common gas cavity 139 are illuminated by two different wavelengths obtained by a lamp 134 and two different interference filters 132 and 133, such that the two wavelengths are substantially equal in intensity, but one wavelength is absorbed by the gas 131 to be directly sensed, and the other wavelength is not. A first electrical signal is taken from array 128, comprising a fixed signal caused by impingement and absorption of radiation on sensors 130 together with a signal component dependent upon the concentration of the gas to be directly sensed. A second electrical signal is taken from array 129, comprising only a fixed signal caused by impingement and absorption of radiation on sensors 130. The two signals are taken via leads 136 and 135 respectively, to a differential amplifier 137 shown in FIG. 6(d), producing a subtracted signal 138 in which the fixed signal caused by impingement and absorption of radiation on sensors 130 is substantially removed.

In the differential approaches shown in FIGS. 6(a) through 6(d), the magnitude of the second signal may be used as a measure of the intensity of the radiation source, so that changes in the intensity of the radiation source may be detected and the signals corrected accordingly.

As in the non-differential approaches, the thermal sensors used in the differential approach may also be provided with radiation masks, or coated with reflective metal layers, to minimize direct impingement and absorption of infrared radiation.

Figure 2:
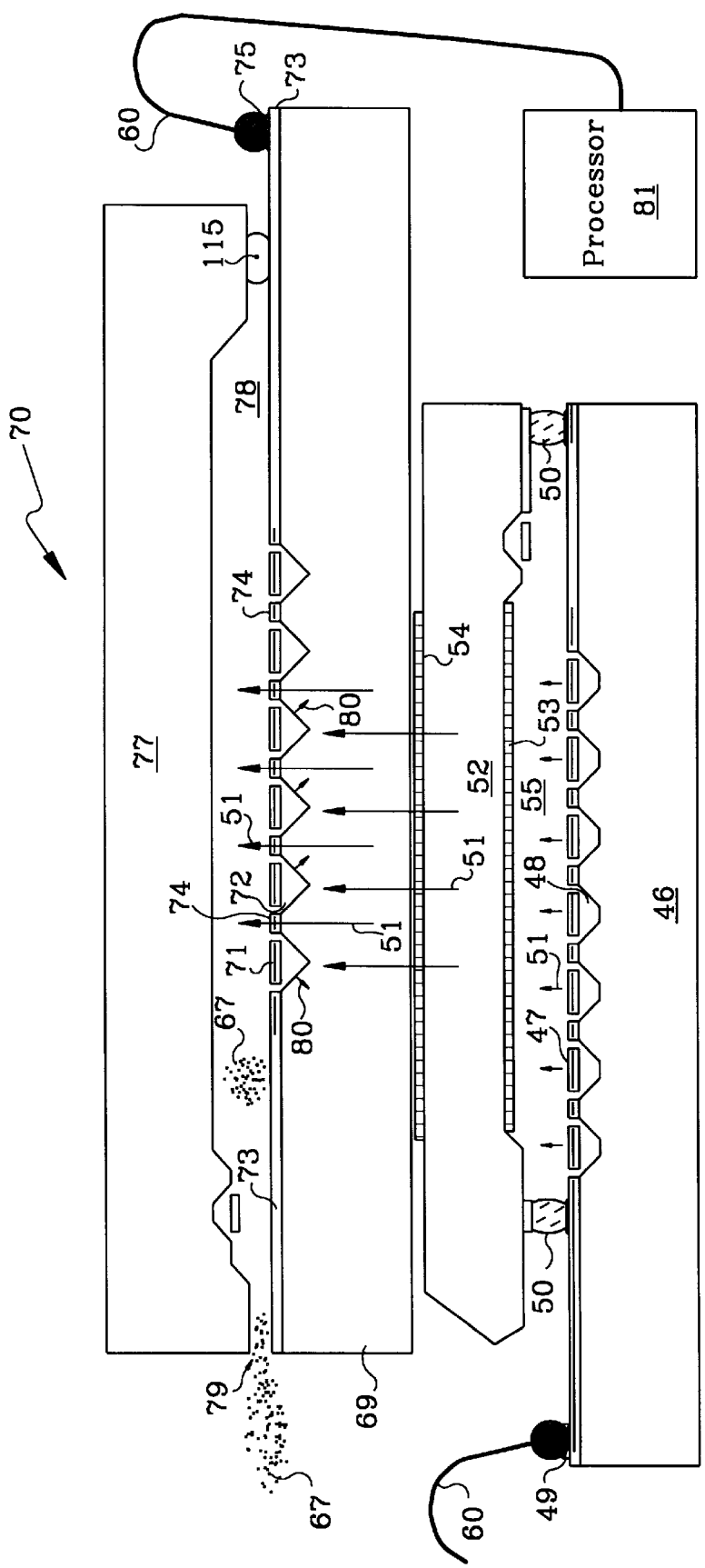
FIG. 2 shows another design of an inferential opto-thermal gas sensor.

FIG. 2 is a cross-section diagram of an opto-thermal gas sensor 70 with radiation passing in an opposite direction. Silicon wafer 46 is about 5×5 millimeters (mm) square and about 20 mils thick. Wafer 46 has formed on it a heated radiation source 47 of IR radiation. Source 47 is fabricated from a high refractory material such as silicon nitride with resistive heating materials. Grooves or pits 48 are etched in wafer 46 to minimize heat loss from source 47. Leads 60, about one mil thick, are attached to contacts 49 for providing an AC signal at a frequency from 10 to 100 hertz to activate source 47 so as to emanate radiation 51. Attachment materials 50 are formed on the periphery of chip or wafer 46. A silicon wafer 52 about 20 mils thick is attached in a vacuum, so that space 55 is evacuated of air. An AR film coating 53 is formed on a first side of wafer 52 and a narrow band pass IF multiple stack layer 54 for passing 4.3 microns of light is formed on a second side of wafer 52. AR film layer 53 is about 2 to 6 films of quarter wavelength thicknesses of alternating materials having different indices of refraction. IF layer 54 is a stack of half wavelength films of alternating materials having different indices of refraction. Wafer 52 is brought into proximity with wafer 46 upon contact of attachment materials 50 on wafer 46 at a peripheral surface of wafer 52 to form an evacuated thermally isolating space 55.

The heated radiation source 47, being within 1 to 2 microns of the solid Si substrate, has a fast response, is modulated at as high a frequency as possible (typically 10 to 100 hertz) and fills the cavity with light, which is essential to obtain high sensitivity. If light source 47 were to be an incandescent mini-tungsten filament lamp, the maximum pulse rate of the AC excitation signal would be about 10 hertz. Increased frequency results in better sensitivity since low-frequency electronic noise is less present. The present integrated circuit light source 47 can effectively be cycled or pulsed up to 100 hertz which results in improved sensitivity of sensor 70.

A silicon detector wafer 69 is formed with a first surface on 4.3 micron narrow band pass optical interference filter 54 and silicon wafer 52. Wafer 69 has grooves or pits 72 formed or etched on a second surface of wafer 69 for reflection of radiation 51 and for improved thermal contact of elements 71 with the gas. A thermo-electric (TE) temperature sensor or detector layer 73 is formed on wafer 69. Temperature sensitive elements 71 are formed over pits 72. Elements 71 are coated with reflective metal to minimize direct absorption of infrared radiation. Temperature insensitive and radiation 51 transparent portions 74 of sensor layer 73 are formed on the non-etched portions of the second surface of wafer 69. Electrical contacts 75 are formed on detector layer 73 for electrical signal transmission to and from layer 73 via leads 60. Attachment materials 115 are formed on the periphery of layer 73 and the second surface of wafer 69. A top cap silicon wafer 77 is formed and attached to form cavity 78. The attachment is such that at one or more vias, channels or holes 79 are formed such that gas and/or air can enter cavity 78.

The functioning of opto-thermal gas sensor 70 includes the emission of fluctuating or pulsing radiation 51 having an IR component. Light 51 goes through AR layer 53 and through wafer 52 to IF layer 54. A portion of light 51 is filtered out by narrow band pass film layer 54 which passes only light having a wavelength of, for example, 4.3 microns (for $CO_2$ detection). Filters with other band pass wavelengths may be used depending upon the type of gas or fluid that is to be detected. The 4.3 micron portion of the light enters wafer 69. Virtually all of light 51 that impinges pits 72 is reflected as light 80. Light 51 that impinges the non-etched portions of the second surface of wafer 69 passes through detector portions 74 into cavity 78. Pits 72 reflect light 51 so that temperature sensitive portions 71 are not affected by heat of the incoming light 51. Air and/or gas 67, such as $CO_2$, flows into and through cavity 78 via channels 79. Light 51 is absorbed by $CO_2$ which heats up and causes sensors 71 to heat up and result in the detection of heat and consequently the presence of $CO_2$, since the wavelength of light 51 and the absorption wavelength of $CO_2$ are the same. As gas 67 passes through and is present in cavity 78, light 51 is fluctuating or pulsing in magnitude or intensity and causing the $CO_2$ of gas 67 to heat and cool. Electrical signals from detector elements 71 go to a processor 81 via contacts 75 and leads 60. Processor 81 determines the presence and the amount of $CO_2$ and inferentially indicates the presence of toxic gases present in the immediate environment of gas sensor 70. Reflected light 80 is kept from sensor elements 71 to minimize fixed signals going to processor 81. A differential arrangement like that of FIGS. 6a, 6b, 6c and 6d may be employed. Alterations of sensor 70 may be made like those to sensor 10 to directly sense other kinds of gases or liquids.

Gas sensor 70 may be designed to directly detect and indicate the presence of other gases or liquids besides $CO_2$. Narrowband pass filter 54 would be changed to a filter that would pass a different wavelength of light 51 which would be equivalent to the absorption wavelength of the other kind of gas to be detected and measured. For instance, filter would be designed to pass 4.6 micron wavelength of light if CO were to be directly detected by sensor 70 or to a wavelength from 3.2 to 3.4 microns if a gas or liquid (VOCs) having hydrocarbon (CH) bonds were to be directly detected by sensor 70.

Figure 3:
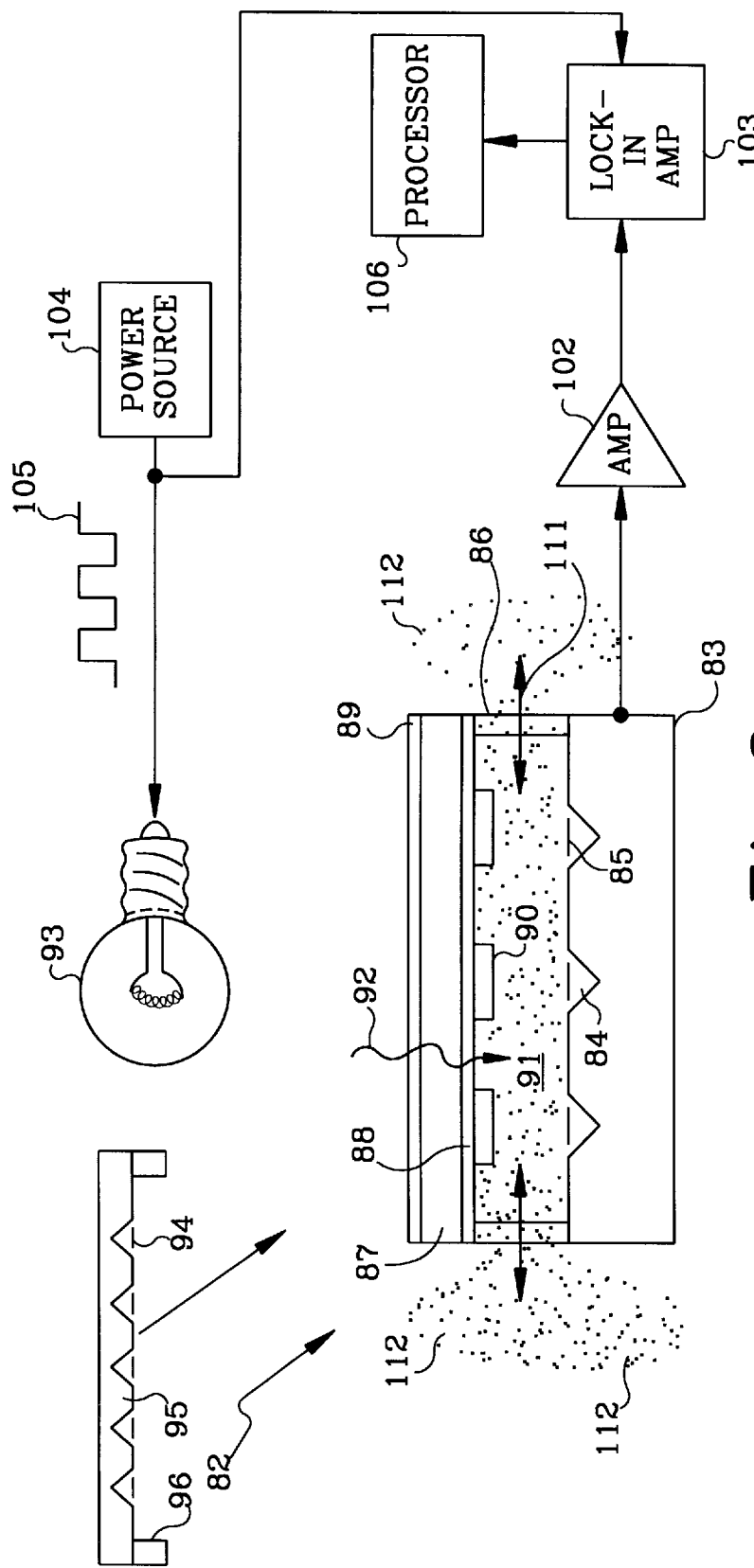
FIG. 3 is of still another design of an opto-thermal gas sensor.

FIG. 3 illustrates another opto-thermal gas sensor 82. A silicon substrate 83 has etch pits 84. Situated over etch pits 84 are thermoelectric receptors 85. Situated on substrate 83 are spacers 86. On spacers 86 is a silicon substrate 87. Formed on one surface of substrate 87 is a narrow band pass interference filter 88. Formed on the other planar surface of substrate 87 is anti-reflective film 89. Formed on filter 88 are shadow masks 90 which block incoming light coming through film 89, substrate 87 and filter 88 into cavity 91, but only in areas directly over thermoelectric sensors 85. The purpose of each shadow mask 90 is to largely block light 92 coming into cavity 90 from impinging on sensor elements 85. The source of radiation or light 92 may be from an incandescent light bulb 93 or a microemitter array 94 formed on a source substrate or wafer 95. Spacers 96 may be formed on substrate 87 or film 89 to support substrate or wafer 95 containing light or radiation source elements 94. Substrate 95 supported by spacers 96, when formed on wafer 87 or film 89, results in a thermal isolation cavity between wafer 95 and wafer 87 or film 89.

Light 92 from either microemitters 94 or light bulb 93, is modulated with a varying intensity or a pulse waveform. Light 92 goes through thermal isolation cavity 97 if microemitters 94 are used, or initially goes through antireflective film 89 if light bulb 93 is used. After light 92 goes through film 89, substrate 87 and interference filter 88, it enters cavity 86. Light 92 having wavelengths other than the absorption wavelength of the gas to be detected is blocked by narrow band pass filter 88. Light of all wavelengths is blocked by shadow mask 96 to reduce impingement of light 92 on thermal sensors 85. Thermal sensors 85 may be coated with a reflective metal layer to minimize direct absorption of infrared radiation. Air and/or gas 112 of the ambient environment about sensor 82 is free to have a flow 111 in and out of cavity 91. If gas 112 having an absorption wavelength that is the same as the wavelength of light 92 that passes through filter 88, then light 92 is absorbed by that gas 112 and as a result heats up. The increase of temperature of gas 112 is detected by thermal sensors 85. If there is no gas having an absorption wavelength which is the same as the wavelength of light 92 passing through filter 88, then there is no absorption of the light by the gas and no increase or change of the temperature of the gas and/or air within cavity 91. Therefore, thermal sensors 85 detect no change in temperature. However, if shadow masks 90 were not present, then light 92 would impinge thermal sensors 85 which would detect increases and/or changes in temperature in cavity 91, thereby providing a large fixed signal in addition to the gas-dependent signal.

FIGS. 4a, 4b and 4c illustrate the effects of light 92 in cavity 91 with and without shadow mask 90 and metal reflective layers. Waveform of FIG. 4a reveals the amplitude of light 92 coming through filter 88 into chamber 91. FIG. 4b shows a signal 99 from thermal sensor 85 when shadow mask 90 is not present. If there is a gas in chamber 91 having an absorption wavelength, which is the same as that of the light 92 passing through interference filter 88, then increased heat in the chamber as a result of the absorption of light 92 by the gas being detected is superimposed as curve 100 on curve 99. With the shadow mask 90 in place, and with a reflective layer, signal 99 is largely removed due to the blocking of light 92 from impinging on and being absorbed by thermal sensors 85. The resultant sensor signal with sensor 85 isolation from light 92, results in signal 100 shown in FIG. 4c.

Signals from sensors 85 go to amplifier 102 and onto a lock-in amplifier 103. Power source 104 outputs an electrical signal 105 which is provided to light bulb 93 or microemitters 94 to result in light 92 of a pulsed or varying intensity. Also, signal 105 is fed to lock-in amplifier 103. A signal output of lock-in amplifier 103 provides an indication of the amount of concentration of the gas detected in cavity 91 and about the ambient environment of sensor 82. The signal from amplifier 103 goes to processor 106 which inferentially determines from the amount of a directly detected gas, for example, $CO_2$, the presence and amounts of various toxic gases that are in the ambient environment immediately around and about the micromachined inferential toxic gas indicator 82. Processor 106 also infers present or past chemical or physical activity around sensor 82. It also may portend future chemical or physical activity. Processor 106 may have a table of information that indicates certain amounts of concentrations of particular gases or fluids that infer the presence of certain amounts of concentrations of other gases or fluids. The presence of certain amounts of concentrations of other gases or fluids are more accurately inferred by the presence of certain amounts of concentrations of the particular gases or fluids in cavity 91 because the amounts of the detected concentrations, such as $CO_2$, are up to several magnitudes larger than the certain amounts of concentrations of the other inferred gases or fluids.

FIG. 5 shows the fabrication of thermo-electric sensor 85. Silicon substrate 83 has an edge pit 84 for purposes of thermal isolation of detector 85. A micromachined array of thermal electric sensors 85 are formed from overlapping thin film metals 107 and 108. They are formed between layers of silicon nitride 109 which is formed on silicon substrate 83. The sensor portion of metal layers 107 and 108 are isolated to the areas of overlap and contact between metals 107 and 108, which are situated over etch pits 84, which cuts 110 define. A metal reflective layer (gold) may be applied (109a) to reduce direct absorption of radiation by the thermoelectric sensor 85.

I claim:

1. A micromachined integrated circuit gas/fluid sensor comprising:

a first wafer;

at least one microemitter formed on a first surface of said first wafer;

a second wafer having a first surface proximate to said at least one microemitter, and enclosing a vacuum;

a narrow band pass filter for a first wavelength formed on a second surface of said second wafer;

a third wafer having a first surface proximate to said narrow band pass filter;

a plurality of pits formed on a second surface of said third wafer, wherein each pit of said plurality of pits substantially reflects radiation impinging the pit;

a plurality of areas formed in the second surface of said third wafer, wherein each area substantially transmits radiation of the first wavelengths;

a plurality of thermal sensors proximate to the second surface of said third wafer wherein each thermal sensor of said plurality of thermal sensors is situated over a pit of said plurality of thermal sensors;

a fourth wafer having a first surface at a distance from but adjacent to said plurality of thermal sensors and the second surface of said third wafer to form a cavity having an opening so that a gas or fluid from the ambient environment about the sensor may enter and/or exit the cavity.

2. The sensor of claim 1 further comprising:
a first through-the-wafer contact formed on a second surface of said first wafer and through said first wafer to said at least one microemitter; and
a second through-the-wafer contact formed on a second surface of said first wafer and through said first, second and third wafers to said plurality of thermal sensors.

3. The sensor of claim 2 further comprising an integrated circuit formed on the second surface of said first wafer.

4. The sensor of claim 3 further comprising an antireflective coating formed on the first surface of said second wafer.

5. The sensor of claim 4 wherein:
radiation that may come from said at least one microemitter and pass through the antireflective coating, said second wafer, said narrow band pass filter, a first portion of the radiation from said narrow band pass filter will be reflected by said plurality of pits formed on the second surface of said third wafer, and a second portion of the radiation from said narrow band pass filter will pass through said third wafer where none of said plurality of pits is formed;
gas or fluid in the cavity impinged by radiation passing through said third wafer will change in temperature if the gas or fluid has an absorption wavelength at the first wavelength;
gas or fluid in the cavity impinged by radiation passing through said third wafer will change in temperature by a substantially fixed amount if the gas or fluid has an absorption wavelength not at the first wavelength, and will vary in temperature by an increased amount if the gas or fluid does have an absorption wavelength at the first wavelength, and will vary in temperature by an increased amount if the gas or fluid does have an absorption wavelength at the first wavelength; and
said plurality of thermal sensors can sense a change of temperature of the gas or fluid.

6. The sensor of claim 5 wherein:
said plurality of thermal sensors outputs a signal that indicates a magnitude of the change of temperature of the gas or fluid;
the magnitude of the change of temperature indicates an amount of concentration of the gas or fluid in the cavity and in turn in the ambient environment of the gas/fluid sensor.

7. The sensor of claim 6 further comprising a processor wherein:
the signal from said plurality of thermal sensors, indicating an amount of concentration of the gas or fluid having an absorption wavelength at the first wavelength, goes to said processor; and
said processor process the signal from said detector and provides inferred information indicative of a presence of other gases or fluids and/or future or present or past chemical or physical activity.

8. The sensor of claim 7 wherein:
said processor comprises a table of information that indicates certain amounts of concentrations of particular gases or fluids infer the presence of certain amounts of concentrations of other gases or fluids; and
the presence of certain amounts of concentrations of other gases or fluids are more accurately inferred by the presence of certain amounts of concentrations of the particular gases or fluids because the latter amounts of concentrations are up to several magnitudes larger than the certain amounts of concentrations of other gases or fluids.

9. The sensor of claim 8 wherein:
the first wavelength is at an absorption wavelength of $CO_2$; and
the presence of $CO_2$ indicates the presence of certain combustion products.

10. A micromachined integrated circuit gas/fluid sensor comprising:
at least one microemitter formed on semiconductor material;
a filter for a first wavelength formed on the semiconductor material proximate to said at least one microemitter;
a plurality of pits formed in the semiconductor material, proximate to said filter, wherein each pit of said plurality of pits substantially reflects radiation impinging the pit;
a plurality of thermal sensors wherein each thermal sensor of said plurality of thermal sensors is situated over a pit of said plurality of thermal sensors; and
a cavity formed in the semiconductor material adjacent to said plurality of thermal sensors, wherein said cavity has an opening so that a gas or fluid from an ambient environment about the sensor may enter and/or exit said cavity.

11. The sensor of claim 10 wherein:
radiation that may come from said at least one microemitter, pass through said filter, a first portion of the radiation from said filter will be reflected by said plurality of pits, and a second portion of the radiation from said filter will pass through a plurality of areas proximate to said plurality of pits;
gas or fluid in said cavity impinged by radiation will change in temperature if the gas or fluid has an absorption wavelength at the first wavelength;
gas or fluid in said cavity impinged by radiation will change in temperature by a substantially fixed amount if the gas or fluid has an absorption wavelength not at the first wavelength, and will vary in temperature by an increased amount if the gas or fluid does have an absorption wavelength at the first wavelength, and will vary in temperature by an increased amount if the gas or fluid does have an absorption wavelength at the first wavelength; and
said plurality of thermal sensors can sense a change of temperature of the gas or fluid.

12. The sensor of claim 11 wherein:
said plurality of thermal sensors outputs a signal that indicates a magnitude of the change of temperature of the gas or fluid; and
the magnitude of the change of temperature indicates an amount of concentration of the gas or fluid in the cavity and in turn in the ambient environment of the gas/fluid sensor.

13. The sensor of claim 12 further comprising a processor wherein:
the signal from said plurality of thermal sensors, indicating an amount of concentration of the gas or fluid having an absorption wavelength at the first wavelength, goes to said processor; and
said processor processes the signal from said detector and provides inferred information indicative of a presence of other gases or fluids and/or future or present or past chemical or physical activity.

14. The sensor of claim 13 wherein:
said processor comprises a table of information that indicates certain amounts of concentrations of particular gases or fluids, which infer the presence of certain amounts of concentrations of other gases or fluids; and the presence of certain amounts of concentrations of other gases or fluids are more accurately inferred by the presence of certain amounts of concentrations of the particular gases or fluids because the latter amounts of concentrations are up to several magnitudes larger than the certain amounts of concentrations of other gases or fluids.

15. The sensor of claim 14 wherein:

the first wavelength is at an absorption wavelength of $CO_2$; and the presence of $CO_2$ indicates the presence of certain combustion products.

16. The sensor of claim 15 further comprising an integrated circuit formed on the semiconductor material.

17. The sensor of claim 16 wherein the integrated circuit comprises said processor.

18. A micromachined integrated circuit gas/fluid sensor comprising:

at least-one microemitter formed on semiconductor material;

a filter for a first wavelength formed on the semiconductor material proximate to said at least one microemitter;

at least one pit formed in the semiconductor material, proximate to said filter, wherein said at least one pit substantially reflects radiation impinging the pit;

at least one thermal sensor situated over said at least one pit; and a cavity formed in the semiconductor material, adjacent to said at least one thermal sensor, wherein said cavity has at least one opening so that a gas or fluid from an ambient environment about the sensor may enter and/or exit said cavity.

19. The sensor of claim 18 wherein:

radiation that may come from said at least one microemitter and pass through said filter, a first portion of the radiation from said filter will be reflected by said at least one pit, and a second portion of the radiation from said filter will pass through an area proximate to said at least one pit;

gas or fluid in said cavity impinged by radiation will change in temperature if the gas or fluid has an absorption wavelength at the first wavelength;

gas or fluid in said cavity impinged by radiation will change in temperature by a substantially fixed amount if the gas or fluid has an absorption wavelength not at the first wavelength, and will vary in temperature by an increased amount if the gas or fluid does have an absorption wavelength at the first wavelength, and will vary in temperature by an increased amount if the gas or fluid does have an absorption wavelength at the first wavelength; and said at least one thermal sensor can sense a change of temperature of the gas or fluid.

20. The sensor of claim 19 wherein:

said at least one thermal sensor outputs a signal that indicates a magnitude of the change of temperature of the gas or fluid; and the magnitude of the change of temperature indicates an amount of concentration of the gas or fluid in the cavity and in turn in the ambient environment of the gas/fluid sensor.

21. The sensor of claim 20 further comprising a processor wherein:

the signal from said at least one thermal sensor, indicating an amount of concentration of the gas or fluid having an absorption wavelength at the first wavelength, goes to said processor; and said processor processes the signal from said at least one thermal sensor and provides inferred information indicative of a presence of other gases or fluids and/or future or present or past chemical or physical activity.

22. The sensor of claim 21 wherein:

said processor comprises a table of information that indicates certain amounts of concentrations of particular gases or fluids, which infer the presence of certain amounts of concentrations of other gases or fluids; and the presence of certain amounts of concentrations of other gases or fluids are more accurately inferred by the presence of certain amounts of concentrations of the particular gases or fluids because the latter amounts of concentrations are up to several magnitudes larger than the certain amounts of concentrations of other gases or fluids.

23. The sensor of claim 22 wherein:

the first wavelength is at an absorption wavelength of $CO_2$; and the presence of $CO_2$ indicates the presence of certain combustion products.

24. The sensor of claim 23 further comprising an integrated circuit formed on the semiconductor material.

25. The sensor of claim 24 wherein the integrated circuit comprises said processor.

* * * * *